United States Patent [19]

Riva et al.

[11] 4,425,924

[45] Jan. 17, 1984

[54] BLOOD VELOCITY MEASUREMENT IN RETINAL CAPILLARIES UTILIZING THE BLUE FIELD ENTOPTIC PHENOMENON

[76] Inventors: Charles E. Riva; L. Benno Petrig, both of Myrin Cir., 51 N. 35th St., Philadelphia, Pa. 19104

[21] Appl. No.: 306,699

[22] Filed: Sep. 29, 1981

[51] Int. Cl.³ .............................................. G01P 3/36
[52] U.S. Cl. .................................... 128/745; 128/691
[58] Field of Search ...................... 128/637, 691, 745; 356/39; 364/555, 578

[56] References Cited

U.S. PATENT DOCUMENTS 4,166,695 9/1979 Hill et al. .......................... 128/691
4,331,132 5/1982 Mukasa ............................. 128/691
4,346,991 8/1982 Gardner et al. .................... 128/691

Primary Examiner—Kyle L. Howell
Assistant Examiner—George Yanulis
Attorney, Agent, or Firm—Robert C. Podwil

[57] ABSTRACT

A method for determining the speed of leukocytes in retinal capillaries comprises the steps of simulating, by means of a minicomputer system which includes a visual display, the motion of entoptically seen leukocytes in retinal capillaries; observing entoptically the motion of actual leukocytes in the retinal capillaries of the subject's own eye; and comparing the appearances and motions of the visual display and the actual leukocytes. Apparatus for performing such a method comprises a minicomputer, a graphic display, and a display—processor interface.

17 Claims, 9 Drawing Figures

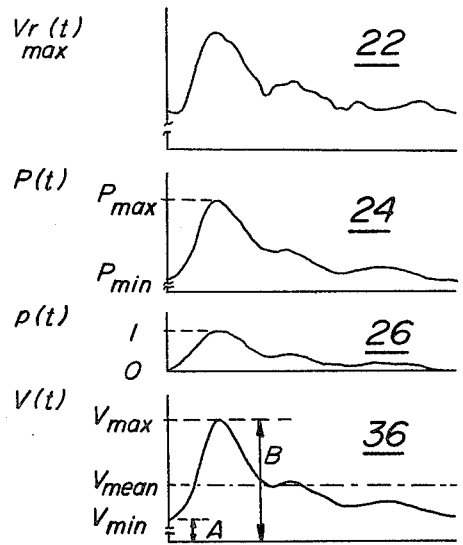
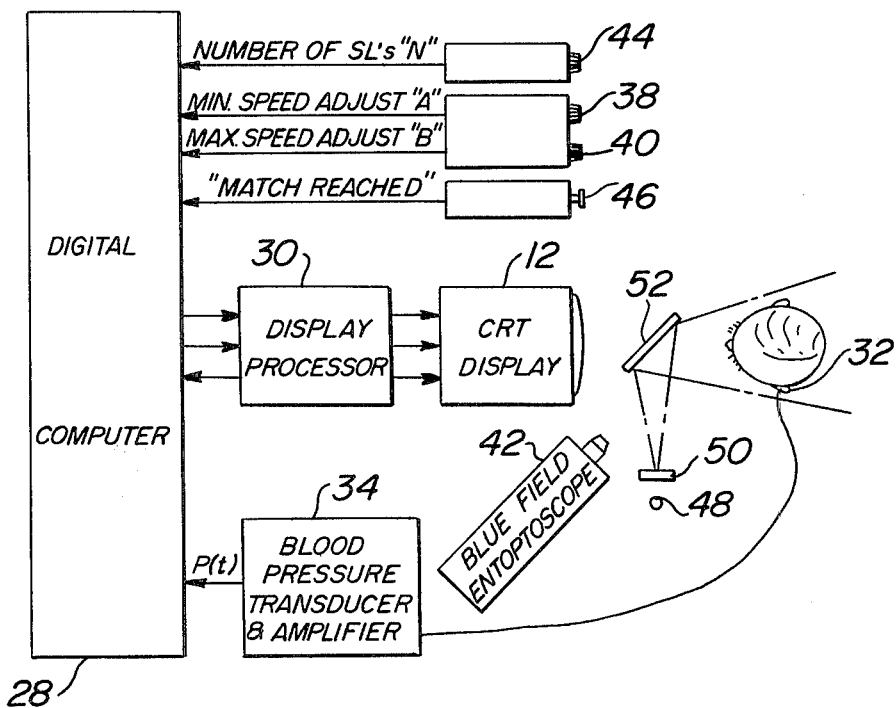
FIG. 4
FIG. 5

| COMMAND MNEMONIC | COMMAND WORD | | |
|---|---|---|---|
| | CODE 16    11 | DATA 10           1 | |
| LDX | 0 0 1 | | LD: LOAD |
| LDY | 0 1 0 | | X: X-COORDINATE BUFFER |
| LDZ | 0 1 1 | | Y: Y-COORDINATE BUFFER |
| LDX&I | 1 0 1 | | Z: INTENSITY BUFFER |
| LDY&I | 1 1 0 | | I: INTENSIFY |
| LDZ&I | 1 1 1 | | &: AND AT THE SAME TIME |

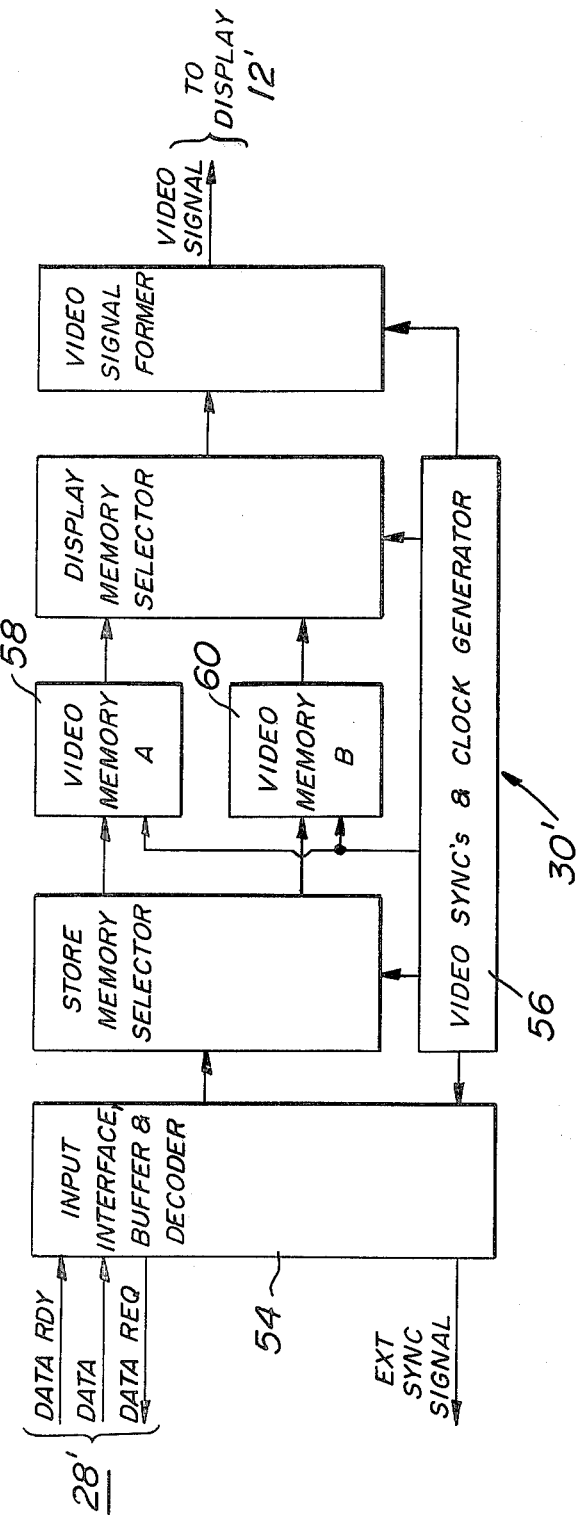

BLOOD VELOCITY MEASUREMENT IN RETINAL CAPILLARIES UTILIZING THE BLUE FIELD ENTOPTIC PHENOMENON

BACKGROUND OF THE INVENTION

This invention relates to a method and apparatus for measuring retinal blood velocity in retinal capillaries utilizing the so-called "blue field entoptic phenomenon." "Entoptic" (i.e., within one's own eye) phenomena are visual perceptions of normal and abnormal structures in one's own eye.

Determining retinal blood flow is fundamental to an understanding of certain basic physiologic processes and pathologic conditions in the eye, and to evaluating objectively the treatment of certain ocular diseases. Quantitative measurement of retinal blood velocity and flow in the capillaries can be of particular importance. It is believed that the velocity of leukocytes in retinal capillaries is proportional to the flow of whole blood in these vessels. (Riva, Sinclair and Grunwald, Invest. Ophthalmol. & Vis. Sci. 21:34–38, 1981). At present, however, very little is known about the hemodynamics in retinal capillaries because of the lack of adequate measurement techniques.

The blue field entoptic phenomenon is the perception of one's own leukocytes (white blood cells) flowing in the macular capillaries of the retina. Vierordt, in 1860 (K. Vierordt, Grundriss der Physiologie (Meidinger, Frankfurt, 1860), suggested that the speed of blood flowing in retinal capillaries could be determined by measuring the speed of the leukocytes that one sees by means of the blue field entoptic phenomenon. Pursuing this idea, Kato (K. Kato, "The velocity of the blood stream in the retinal capillaries of the human eye. (The variation of the velocity of the blood stream after standing)," Acta. Soc. Ophthalmol. Jpn. 55, 1070–1078 (1971) Japanese) calculated the speed of the leukocytes by estimating the time it took the corpuscles to travel the length of a single capillary. In the method described by Hoffman and Podestà (D. H. Hoffmann and H. H. Podestà, "Zur Messung der Strömungsgeschwindigkeit in kleinsten Netzhautgefässen," Acta, XX Concilium Ophthalmologicum Germania, 1966. Edited by Weigelin E. Excerpta Medica, 1, 162–164 (1966)), subjects were asked to count the number of leukocytes that passed through one capillary in 30 seconds. Blood flow was determined from that number of leukocytes and their concentration in the blood.

The passage of leukocytes through a single macular capillary is difficult to observe for a prolonged time (M. Sint, E. Riehm and H. H. Podestà, "Untersuchungen über die Beziehungen der zentralen kapillaren Retinadurchblutung zur Augendruckhöhe bei Glaucompatienten mit Hilfe der entoptisch sichtbaren Blutbewegung," Klin. Mbl. Augenheilk., 171, 743–753 (1977). As a result, therefore, neither of the above-mentioned methods has become a routine clinical tool in retinal circulation examinations.

This invention relates to a novel method and apparatus for measuring the speed of leukocytes in retinal capillaries, the use of which eliminates the need for accurate tracking of a single capillary. The present method and apparatus calls on subjects to compare and match the appearance of the "global" motion of computer-simulated leukocytes with the appearance of the global motion of their own leukocytes, observed entoptically.

It is an object, therefore, of this invention to provide a novel method and apparatus for measuring quantitatively retinal blood velocity and flow, using the blue field entoptic phenomenon.

It is another object to provide a method and apparatus for measuring quantitatively retinal blood velocity and flow and which obviates the need for observing any single macular capillary for a prolonged time.

It is yet another object of this invention to provide a noninvasive and relatively quick method for measuring quantitatively retinal blood velocity and flow.

Other objects will appear hereinafter.

SUMMARY OF THE INVENTION

The above and other objects of this invention are realized, in a presently preferred form of the invention, by a method which, in general, comprises the steps of simulating by means of a visual display the appearance and motion of entoptically seen leukocytes in retinal capillaries; observing entoptically actual leukocytes in one's own retinal capillaries; and comparing and matching the appearance and motion of the simulated leukocytes with the entoptically perceived leukocytes. Because, in a given display, the velocity of the simulated leukocytes is known, correspondence of the display and the actual leukocytes is indicative of the speed of the actual leukocytes.

In a presently preferred form of the apparatus, the number and speed (maximum and minimum) of the simulated leukocytes can be adjusted by the subject, and the simulated leukocytes can be given the appearance of pulsatile velocity through the use of a blood pressure wave sensed from the subject.

In its apparatus aspect, one presently contemplated form of the invention utilizes a cathode ray tube (CRT) display controlled by a digital minicomputer through a display-processor interface. The simulated leukocytes appear as luminous dots on the CRT, against a blue background. The wavelength of the blue background is selected so as to be slightly different from that of the entoptoscope, so that it does not elicit the perception of the blue field phenomenon. Use of this technique is advantageous because, under these conditions, the subject cannot readily distinguish between the simulation and his or her own leukocytes. A possible observational bias is thus avoided.

BRIEF DESCRIPTIONS OF THE DRAWINGS

FIG. 4 is a graphical depiction of a technique for deriving the pulsatile speed of simulated leukocytes, using a blood pressure wave recorded from the earlobe or the fingertip of a subject.

FIG. 5 is a schematic block diagram corresponding to the apparatus of the invention.

Figures 6, 7:
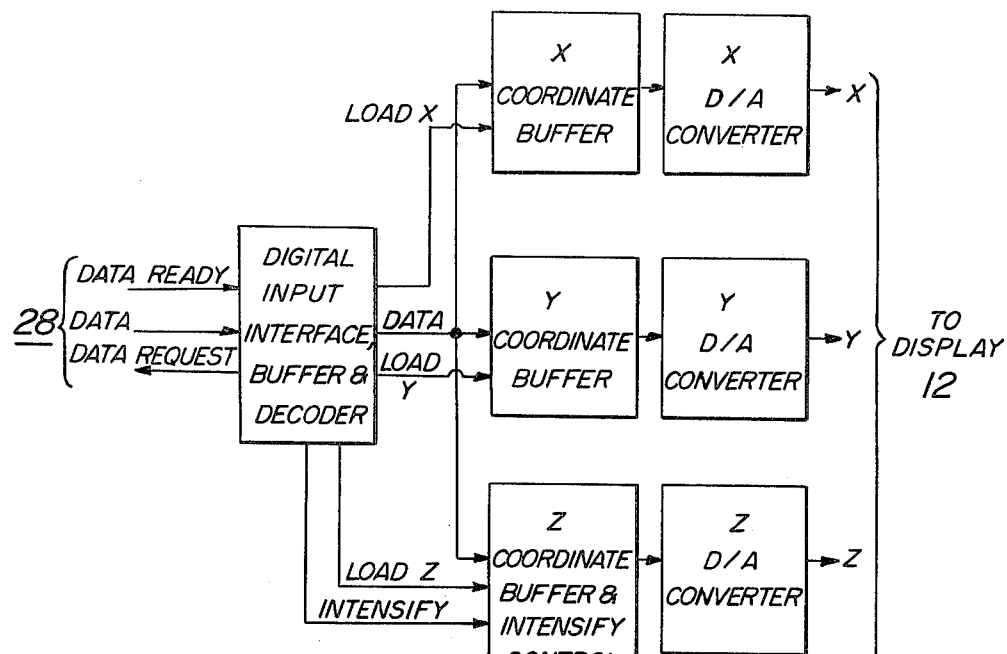
FIG. 6 is a schematic block diagram of a display processor, used in the present invention to generate the display.

FIG. 7 sets forth software commands for the display processor.

Figure 8:
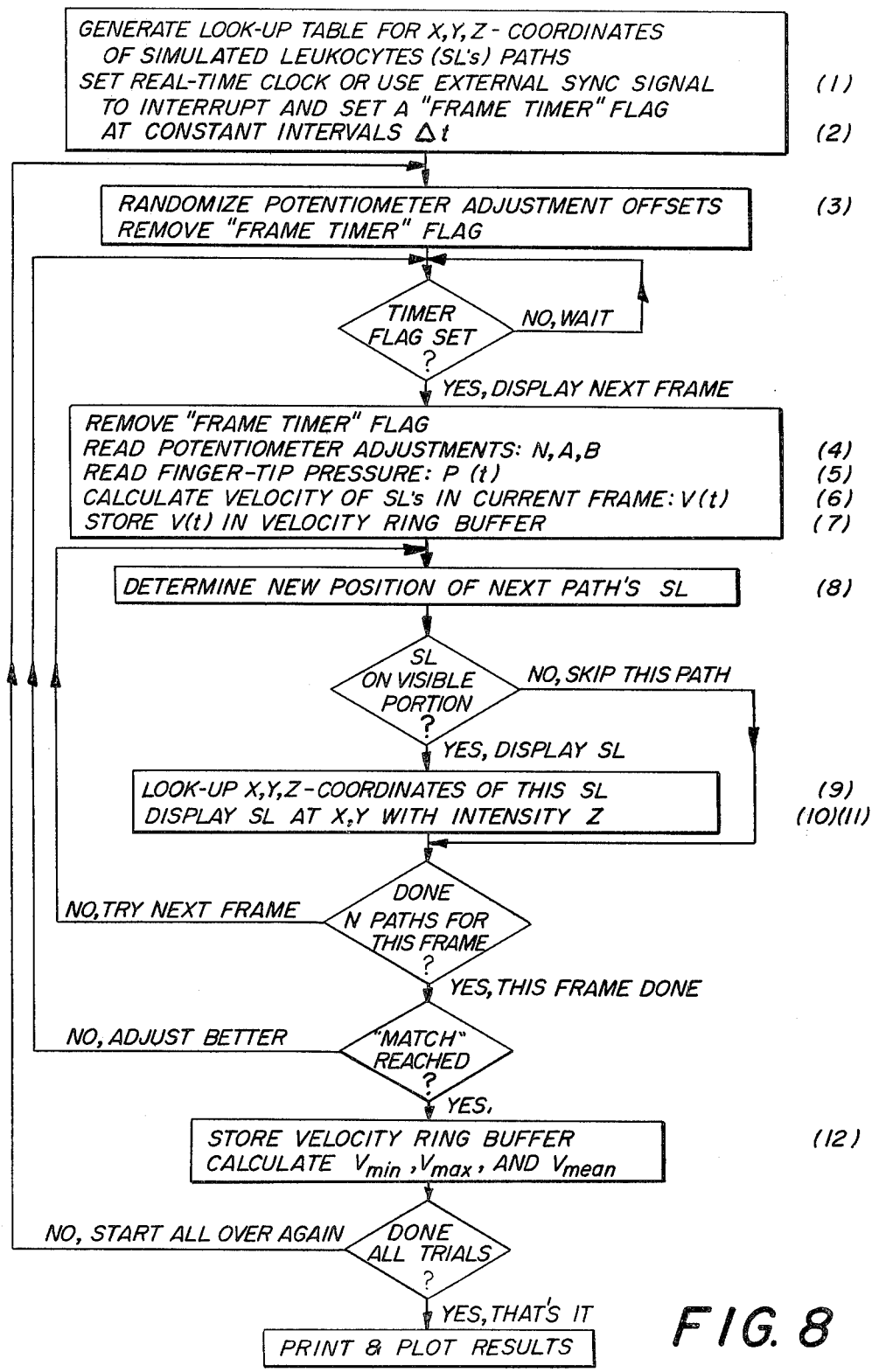

FIG. 8 is a flow chart showing the order of operations which are performed in the simulation of leukocyte motion and performance of the present method.

FIG. 9 is a schematic block diagram of an alternative form of display processor.

DESCRIPTION OF THE PREFERRED EMBODIMENT

Leukocytes in retinal capillaries can be observed remarkably well with an entoptoscope that provides uniform illumination of the retina at a wavelength λ of 430 nm (Δλ=25 nm at half-height) and at a safe intensity level (C. E. Riva, J. J. Kelley, S. H. Sinclair and M. Loebel, "Optical transmismission of cataractous lens at 430 nm and blue field entoptoscopy," Vision Res. 19, 1181-1183 (1979). On close observation, the following characteristics of the leukocyte motion can be noted: (i) the leukocytes appear as dotlike luminous corpuscles with a darker tail; (ii) they move in single file along recurrent, curved paths; (iii) they skirt an area that corresponds to the avascular zone of the retina; and (iv) their speed is normally pulsatile, in phase with the heart cycle: moving quickly forward during systole and slower during diastole.

Referring now to FIGS. 1 through 3 and 5, the manner in which the motion of entoptically seen leukocytes can be simulated will be described.

Figure 2:
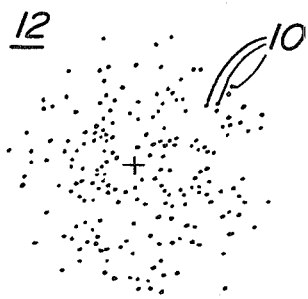
FIG. 2 is an illustration of a representative instantaneous view of simulated leukocytes on the display.

The reference numeral 10 in FIG. 2 designates representative simulated leukocytes ("SL's") as they appear instantaneously on the screen of the display 12 (seen in FIG. 5). The SL's appear as luminous dots on a dark background, and have a diameter, when viewed from a distance, of 55 centimeters of 3.3 minutes of arc. Blue light is added to the background in a manner and for the purpose described below. The cross at the center of the field in FIG. 2 is a fixation target.

Figure 1:
FIG. 1 is an illustration of the representative simulated retinal paths along which simulated leukocytes are "moved" on a visual display in accordance with the invention.

FIG. 1 illustrates the simulated retinal capillary paths 14 upon which the SL's move. It will be understood that these paths are not visible to the subject. The paths 14 are made similar in shape, length and distribution to the capillary loops followed by actual leukocytes observed entoptically.

Referring again to FIG. 1, 200 or more paths 14 of random length are randomly distributed within an annulus A subtending an arc of 8.3° at the distance of 55 cm. An area 16 of about 1.7° arc diameter is left free of paths 14 at the center of the field, to simulate the avascular zone of the macula. Distribution of the paths 14 is otherwise uniform within the annulus.

Figure 3:
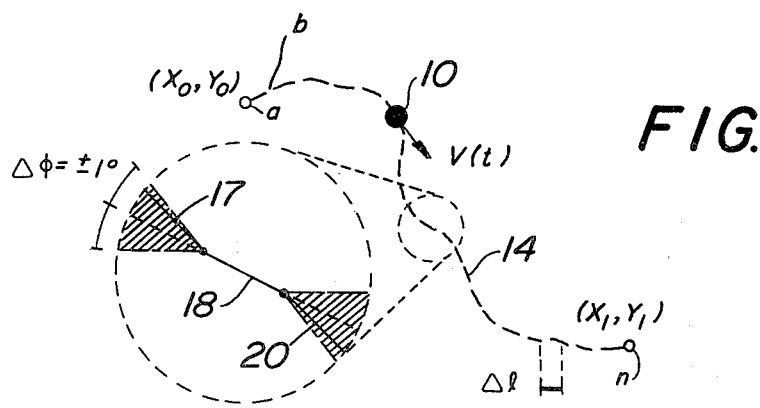
FIG. 3 is an illustration of a single simulated retinal path, partly enlarged, and illustrative of the way in which a simulated path is derived.

Referring now to FIG. 3, which is illustrative of a representative path 14 of a simulated leukocyte 10, the path 14 consists of a random number of discrete points or locations a, b, ... n (between 15 and 25 in number) spaced from each other by a distance of a line element $\Delta l$ in FIG. 3. In order to simulate actual retinal capillaries, each line element 17, 18, 20 of a path 14 is angularly offset from the direction of its adjacent element by an angle $\Delta\phi$ within plus or minus one degree ($\pm 1°$) of the direction of the adjacent element.

All discrete locations a, b, ... n, are stored in a computer memory by their x-y coordinates, but are not displayed.

In one operative embodiment of the apparatus, entopically seen leukocytes were simulated using a Hewlett-Packard 1310A graphics display scope with a fast P4 phosphor cathode ray tube. The display was controlled by a PDP 11-40 minicomputer (with 32K memory) through a display-processor interface described in greater detail below. The speed of motion of the SL's could be varied on-line as is also described in detail below.

The motion of leukocytes in retinal capillaries is perceived as pulsatile by healthy subjects with normal vision. Referring to FIGS. 4 and 5, the manner in which the SL's can be given a simulated pulsatile motion will now be described.

It has been observed that there is a strong similarity between the wave form and phase of the oscillation of a typical normalized blood pressure wave and the variation in systolic-diastolic speed of red blood cells in retinal arteries. Referring to FIG. 4, the reference numeral 22 designates generally a graphic depiction of the variation of the maximum speed $V_r$max of the red blood cells in retinal arteries as a function of time, as recorded by laser Doppler velocimetry (C. E. Riva, G. T. Feke, B. Eberli and V. Benary, "Bidirectional LDV system for absolute measurement of blood speed in retinal vessels," Appl. Opt. 18, 2301-2306 (1979)). The reference numeral 24 designates a graphic depiction of a typical blood pressure wave P(t) recorded from the earlobe or the fingertip. The reference numeral 26 depicts a normalized blood pressure wave $p(t) = [P(t) - P_{min}]/(P_{max} - P_{min})$. Due to the strong similarity between P(t) and the variation in the speed of red blood cells in retinal arteries, a typical earlobe or fingertip pressure wave can be used to generate the desired speed variation of the simulated leukocytes.

Referring now to the block diagram and flow chart of FIGS. 5 and 8, the x and y coordinates of the simulated leukocytes are stored in the memory of a digital computer 28 prior to starting the simulation on the display. During simulation, coordinates are selectively transmitted to the display processor 30, which in turn transforms the digital coordinates into the appropriate form to be displayed on the display 12.

In a manner somewhat similar to that of a television image, the simulation of moving leukocytes appears as a series of frames in rapid succession. The frame rate, however, in the present system, can be varied according to the speed of calculation of the computer and the total number of simulated leukocytes per frame selected. Frame rate is controlled by means of a real time clock incorporated into the computer 28, and the range of practical frame rates, it has been found, is on the order of 25 to 100 frames per second. In operation of the apparatus and the method, the frame rate is held constant by means of the clock.

Since the time between two successive frames is a constant $\Delta t$, the velocity of a SL traveling on its defined path is proportional to the distance along the path 14 that the SL is moved on the CRT between frames, i.e.,:

$$V = \Delta S / \Delta t.$$

This allows on-line modulation of SL speed by proportionally modulating the displacement of a SL's position at a given frame with respect to its position in the previous frame. Thus, SL's can be made to move according to any given velocity function.

Referring again to FIG. 5, a blood pressure wave P(t) (designated in FIG. 4 by the reference numeral 24) taken from the earlobe 32 or fingertip of a subject is sensed and amplified by a pressure transducer and amplifier 34, and digitized in the computer 28. Then, the digitized P(t) is transformed by software into a normalized function p(t) (designated in FIG. 4 by the reference numeral 26) which has a minimum of 0 and a maximum of unity.

A pulsatile velocity function, in phase with the heart cycle of the subject, can then be constructed according to the formula:

$$V(t)=A+(B-A)p(t).$$

Such a function is depicted graphically in FIG. 4, and designated by the reference number 36.

A and B in the above function are constants which can be adjusted by the subject by means of controls 38 and 40 (potentiometers, for example) seen in FIG. 5.

As has already been explained, the task of a subject consists of comparing the motion of the SL's seen on the display 12 with the motion of leukocytes observed through the blue field entoptic phenomenon. This can be done using the same eye alternately observing the display 12 and a blue field entoptoscope 42. In other situations, for different purposes, the subject (or an observer) may observe the display 12 jnd the entoptoscope 42, one with each eye, either simultaneously or alternately closing one eye.

In the operation of the system shown in FIG. 5, the subject will coarsely adjust the controls 38 and 40 until the entoptic and simulated motions are thought to appear similar.

By means of another control 44, the subject can selectively adjust the number of SL's to equal the number of leukocytes observed entoptically. Finally, the subject can fine-tune the speed of the SL's by again adjusting controls 38 and 40 until the speed of motion and the number of moving particles are thought to appear the same. Pushing of a "match reached" button 46 signals the computer 28 that the motions are same. The computer 28 then stores a ring buffer retaining the function V(t) during the last 5 seconds for later analysis, and calculates the velocity parameters $V_{min}$, $V_{max}$ and $V_{mean}$.

Referring again to FIG. 5, the manner in which blue light is added to the background of the display 12 will now be described. Light from a source 48 passes through a blue filter 50 to a beam splitter 52. The beam splitter 52 may, for example, be a half-silvered mirror disposed in the path of the display 12. The filter 50 is chosen to transmit blue light of a wavelength sufficiently different from that of the entoptoscope not to elicit perception of the blue field phenomenon. The blue light, nevertheless, imparts to the display of simulated leukocytes a background color similar to that seen through the entoptoscope. The similarity makes it difficult for the subject to distinguish the simulated from the entoptically viewed leukocytes, and enhances the ability of the subject to accurately compare and match the appearances of the display and the actual leukocytes.

FIGS. 6 and 7 depict aspects of the display processor hardware and commands.

Referring to FIG. 6, the display processor 30 receives digital data from the computer 28 containing information about, x, y-coordinates and intensity (z) of dots to be displayed on the display 12 to depict leukocytes. Incoming 16-bit words are buffered and decoded. According to the code (bits 14 and 15), either x, y or z coordinate buffer is loaded with data in bits 1–10. Each coordinate is converted to an analog signal suitable for input to the display 12.

With any coordinate load request, an intensification request is optional. Intensification control introduces sufficient delay to account for digital-to-analog converter settling times, and then draws one point on the CRT at current x,y coordinates for a few microseconds. This arrangement allows individual loading of x, y or z coordinates with or without intensification of dots at corresponding display locations. In general, therefore, three data words have to be transmitted for each dot to be displayed; one word for each coordinate x, y and z, with an intensification command supplied together with z.

The timing of transmission of such coordinates for each SL is performed in the computer 28. Such transmission of coordinates must be made to occur repeatedly for every SL in every display frame.

Referring now to FIG. 8, the operation of the method and apparatus may be seen graphically in the form of a flowchart, depicting the following operations:

(1) Generation of x, y coordinates look-up tables:

200 or more randomly curved paths 14 of random length are randomly distributed in an annulus A (FIG. 1) similar to the paths of the entoptically observed leukocytes (FIG. 3). The paths consist of a random number of discrete locations (between 15 and 25), spaced apart from one another by the length $\Delta l$ of a line element, and angularly offset from each other as indicated above.

One SL is assigned to each path 14 and travels along on it according to some velocity function V(t) (FIG. 4) from the beginning of the path ($x_0$, $y_0$) to its end ($x_1$, $y_1$) (FIG. 3). This constitutes the visible portion of the path, $L_v$. An additional hidden portion of the path, $L_h$, is formed by appending a random amount of $\Delta l$'s at the end of each visible path 14, through which the SL must travel, without being displayed, before it can again enter at the beginning of the visible portion of the path 14. Hence, there is a random delay between the disappearance of the SL at ($x_1$, $y_1$) and its reappearance at ($x_0$, $y_0$), depending upon the current velocity function. Some SL's will thus not be displayed in a given display frame. Each SL is assigned an initial position somewhere at random along the displayed or hidden portion of its path.

(2) Timing:

The above-mentioned real-time clock internal to the computer 28 or an external synchronization signal interrupts this program at constant time intervals $\Delta t$ and sets a "frame timer" flag.

(3) Adjustment offsets:

A random offset which is constant during a given trial is added to the adjustment of controls 38, 40 and 44 for the velocity and the number of SL's. This offset is preferably randomly changed before each new trial to prevent subjects from remembering and using a memorized control position.

(4) Velocity function constants:

An analog voltage representing the position of controls 38, 40 and 44 adjusted by the subject is converted to a digital number representative of:

A: minimum velocity;
B: maximum velocity;
N: number of SL paths used for display.

(5) Blood pressure wave:

An analog voltage representing the pressure measured at the subject's earlobe 32 or fingertip is converted to a digital number P(t), the current pressure as a function of time.

(6) Calculation of the velocity function V(t):

Calculate the velocity according to $$V(t) = A + (B-A)p(t) \quad 0 \leq p(t) \leq 1,$$

where
$p(t) = [P(t) - Pmin]/(Pmax - Pmin)$, and
Pmin = Minimum [P(t)],
Pmax = Maximum [P(t)]

(7) Velocity ring buffer:
The velocity ring buffer retains the velocities calculated during the last 5 seconds before the "match reached" button is pressed.

(8) Motion of SL's:
The current position, S(t), of each SL on its path is determined from its position in the previous frame, S(t−Δt), according to $$S(t) = S(t - \Delta t) + \Delta S,$$

where ΔS = V(t)Δt.
Assume lengths of the visible and hidden portions of a path to be $L_v$ and $L_h$ respectively. If S(t) is greater than $(L_v + L_h)$, then the SL has wrapped around the hidden into the visible portion, and we replace S(t) by $S(t) - (L_v + L_h)$.

(9) Locating x, y and z coordinates in look-up tables:
The location of the approximate x, y and z coordinates is given by simply calculating $$K = 1 + S(t)/\Delta l,$$

K: integer number, $1 \leq K \leq 25$, provided that $0 \leq S(t) \leq Lv$.

(10) Displaying a SL:
Display of a SL is accomplished by transmitting the x, y, z (coordinates with an intensity command in the last) to the display processor via a digital output interface.

(11) Sample frame of SL's:
If the display were to be photographed with the shutter open for a time of Δt, the result would be a picture similar to FIG. 2.

(12) Parameter calculations:
Vmin, Vmax and Vmean are calculated from the ring buffer V(t) stored during the last 5 seconds prior to the match: Vmin = Minimum[V(t)], Vmax = Maximum[V(t)], $$V\text{mean} = \frac{1}{T} \int_0^T V(t)dt.$$

(13) Calibration:
Velocities V(t) of the SL's moving on the display 12 are translated to mm's on the retina using geometrical parameters of the eye and the distance between the eye and the scope.

The matching of the motion of the SL's with that of the observed leukocytes is a subjective procedure, and in this sense its accuracy depends upon the reliability of the subject. Control experiments, however, in which subjects were asked prior to the actual test with leukocytes to match the motion of the SL's moving in two separate simulated fields, make it possible to evaluate objectively how accurate a given subject is likely to be able to determine the speed of leukocytes in an actual test.

Three kinds of control experiments were conducted. In the first and second, the number $N_{ref}$ and speed $V_{ref}$ of SL's in the reference field were held constant. The results of these control experiments tended to show that the larger the number of simulated leukocytes in a test field, the more likely it is that they will be perceived as moving faster than they actually are, and vice versa. The control tests also showed that, at least as to some subjects, there is a tendency to perceive the number of simulated leukocytes as being greater than they actually are when the simulated leukocytes are made to move faster. The test results suggest that to increase accuracy, the testing (matching) step should be started with the number ($N_{test}$) and velocity ($V_{test}$) of the SL's significantly higher than the anticipated $N_{ref}$ and $V_{ref}$ values. The simulated values can then alternately be adjusted until the motion of the SL's appears to match those of the observed leukocytes.

In a third control experiment, the number of SL's were maintained the same in both fields, but the speed was made pulsatile. It was shown that, under these conditions, two separate fields of simulated leukocytes can be matched very accurately (less than 10% error in some and less than 20% error in all subjects).

Such values are acceptable for physiological and clinical measurements. Moreover, the average speed of the leukocytes obtained from a group of subjects will most probably be better than ninety percent (90%) accurate, making the method particularly useful for comparing various groups of patients with a group of normal subjects.

Measurements of the speed of leukocytes in retinal capillaries using the present method and apparatus are in good agreement with the data reported by Kato, infra, who found an average speed of 0.77 mm/second. Kato was not able, however, to determine the pulsatile component of the speed, $(V_{max} - V_{min})/V_{min}$. This component was found to be significant in all of a group of five subjects tested by means of the present method and apparatus, and its average for the five subjects was found to be 0.98±0.16.

Experimental data also suggests that the present apparatus and method can most accurately determine $V_{max}$ and $V_{mean}$, and that determination of $V_{min}$ tend to be less accurate.

The present method and apparatus has potential for diagnosing abnormal ocular blood flow caused by eye diseases or by various systemic diseases such as diabetes, systemic hypertension or carotid artery occulations, and for investigating the effect of therapy on retinal circulation.

FIG. 9 illustrates a proposed alternative form of display processor, in which elements corresponding to those previously described are designated by like primed (') reference numerals. In the display processor 30' illustrated in FIG. 9, a color television (TV) monitor 12' is utilized to display the motion of SL's rather than the CRT display 12.

SL's are loaded from the computer 28' by way of an input interface buffer and decoder 54, corresponding to the like element seen in FIG. 6.

Video sync and clock generator circuitry 56 provides video synchronisation signals as well as synchronous readout of intensification data from one of two video memories 58, 60. After every frame, the functions of the two video memories 58, 60 are exchanged. One is ready to be displayed on the screen. The other is ready to accept a new pattern of SL's from the computer via the above-mentioned input interface 54.

The video memory 58 or 60 open to new data storage from the computer 28' is first preset to a uniform background color (e.g. blue) before the SL's are inserted at desired x, y-coordinates. This results in software-hardware interaction identical to the above-described CRT display processor 30. However, a spatial resolution ratio of 4:1 between CRT and TV versions (1024×1024 vs. 256×256 picture elements) is anticipated.

The present invention may be embodied in other specific forms without departing from its spirit or essential attributes, and accordingly, reference should be made to the appended claims as indicating the scope of the invention.

We claim:

1. A method for determining the speed of leukocytes in retinal capillaries comprising the steps of: simulating by means of a visual display the appearance and motion of entoptically seen leukocytes in retinal capillaries, observing the entoptic appearance of actual leukocytes in the retinal capillaries of the subject eye, and comparing and matching the appearances of the display and the actual leukocytes whereby correspondence of the appearances of the display and the actual leukocytes is indicative of the speed of the actual leukocytes.

2. A method in accordance with claim 1, wherein the steps of comparing and matching the appearances of the display and the actual leukocytes are performed by looking into an entoptoscope and at the display.

3. A method in accordance with claim 2, wherein the steps of looking into an entoptoscope and at the display are performed by looking alternately with the same eye into an entoptoscope and at the display.

4. A method in accordance with claim 3, wherein the steps of looking into an entoptoscope and at the display are performed by looking with one eye at the entoptoscope and with the other eye at the display.

5. A method in accordance with claim 4, wherein the entoptoscope and the display are looked at simultaneously.

6. A method in accordance with claim 4 wherein the entoptoscope and the display are looked at alternately.

7. A method in accordance with claim 1, further including the step of selectively varying the speed of the simulated leukocytes provided by the display.

8. A method in accordance with claim 7, wherein the step of selectively varying the speed of the simulated leukocytes is so performed as to vary the maximum and minimum speeds of the simulated leukocytes.

9. A method in accordance with claim 1, further including the step of selectively varying the number of the simulated leukocytes provided by the display.

10. A method in accordance with claim 1, further including the step of selectively varying the speed and number of the simulated leukocytes provided by the display so that the appearance of the display can be selectively altered to approximate the appearance of the actual leukocytes.

11. A method in accordance with claim 10, wherein the steps of comparing and matching the appearances of the display and the actual leukocytes are performed by looking alternately with the same eye into an entoptoscope and at the display.

12. A method in accordance with claim 10, wherein the steps of comparing and matching are performed by looking with one eye at the entoptoscope and with the other eye at the display.

13. A method in accordance with claim 12, wherein the entoptoscope and the display are looked at simultaneously.

14. A method in accordance with claim 12, wherein the entoptoscope and the display are looked at alternately.

15. A method in accordance with claim 10, wherein the step of simulating the appearance of entoptically seen leukocytes includes the further step of providing pulsatile velocities for the simulated leukocytes, the pulsatile velocities having a wave form and phase of oscillation corresponding to a normalized blood pressure wave recorded from the subject.

16. A method in accordance with claim 15, wherein said step of simulating the appearance and motion of entoptically seen leukocytes comprises the further step of observing the display under blue illumination.

17. A method in accordance with claim 15, wherein the step of providing pulsatile velocities for the simulated leukocytes comprises sensing and recording of a blood pressure wave from the subject.

* * * * *